United States Patent [19]

Young et al.

[11] 4,205,096
[45] May 27, 1980

[54] CASE III (C) ADHERENT CONTROLLED RELEASE PESTICIDE

[75] Inventors: Robert W. Young, New York, N.Y.; Samuel Prussin, Carmel, Calif.; Norman G. Gaylord, New Providence, N.J.

[73] Assignee: Young, Prussin, MGK, J.V., New York, N.Y.

[21] Appl. No.: 696,269

[22] Filed: Jun. 15, 1976

[51] Int. Cl.$^2$ .................. A61K 31/695; A01N 17/08
[52] U.S. Cl. .................................... 427/4; 424/77; 424/78; 424/184; 43/136; 424/DIG. 6; 424/DIG. 10; 422/186; 71/DIG. 1
[58] Field of Search .................... 427/4; 424/184, 186, 424/78, 77, DIG. 6, DIG. 10; 71/DIG. 1; 43/136

[56] References Cited

U.S. PATENT DOCUMENTS

| | | | |
|---|---|---|---|
| 2,681,878 | 6/1954 | Kauppi | 424/184 |
| 2,923,095 | 2/1960 | Bordeaux et al. | 427/4 X |
| 2,988,473 | 6/1961 | Mallis | 424/184 |
| 3,151,969 | 10/1964 | Stevens | 424/186 |
| 3,248,409 | 4/1966 | Bluestein | 424/186 |
| 3,375,163 | 3/1968 | Whitney | 424/184 |
| 3,470,292 | 9/1969 | Marschner | 424/184 |
| 3,480,653 | 11/1969 | Pande | 260/429.9 |
| 3,481,768 | 12/1969 | Gowdy | 427/212 |
| 3,590,118 | 6/1971 | Conrady | 424/78 |
| 3,641,239 | 2/1972 | Mohrlok | 424/184 |
| 3,836,647 | 9/1974 | Lange | 424/184 |
| 3,953,591 | 4/1976 | Snyder | 424/78 |

OTHER PUBLICATIONS

Noll Chemistry & Technology of Silicones, pp. 514–515 and 398–399.
C & EN, Oct. 15, 1956, pp. 5060–5063.

*Primary Examiner*—Sam Silverberg
*Attorney, Agent, or Firm*—Roylance, Abrams, Berdo & Farley

[57] ABSTRACT

There are disclosed methods and compositions for the controlled release of insecticides by using a mixture consisting of (a) a hydrolyzable silane or an organopolysiloxane containing hydrolyzable silane groups or partial hydrolyzates thereof, and (b) a pesticide, e.g., an insecticide.

19 Claims, No Drawings

CASE III (C) ADHERENT CONTROLLED RELEASE PESTICIDE

This invention relates to methods and compositions for the controlled release of bioactive agents and, more particularly, to the controlled release of pesticides, such as insecticides.

The utilization of bioactive agents such as pesticides, e.g., insecticides, herbicides and fungicides has become an important fact of life. However, these materials are generally effective only as long as they persist on the substrate to which they are applied.

The basic motivation underlying the modern development of controlled release pesticidal materials has been to extend the duration between applications and thus increase the efficiency and hence economy of control. Controlled release of pesticides permits extended time intervals between treatments and reduction of the dosage, thus reducing environmental impact. Thus, from an ecological standpoint, controlled release of pesticides enhances the lifetime of a non-persistent agent at the site of treatment while maintaining the preferred property of rapid detoxification in the environment surrounding the controlled release pesticide.

The desired controlled release of pesticides has previously been achieved by their incorporation within a polymeric matrix, e.g., encapsulation wherein a pest control agent is surrounded by an enveloping polymeric wall that permits loss through diffusion, permeation or degradation; dispersion of the pesticide in an elastomer or a plastic wherein the pesticide is released through leaching or diffusion; and the chemical combination of the pesticide with a polymer in such a manner that the appended pesticide slowly breaks off the polymeric backbone upon exposure to the pest infested environment. However, the prior art approaches fall short of the desired goal in that there is not adequate provision for the adhesion of the pesticide within the polymeric matrix to the substrate. This permits the removal or transfer of the material from the substrate as a result of physical contact, wind, rain or other atmospheric conditions.

One object of the present invention is to provide a process for the controlled release of bioactive agents such as pesticides.

Another object of the present invention is to improve the adhesion of such an agent to suitable substrates and thus to increase its effective lifetime.

Another object of the present invention is to provide stable compositions which after application to a suitable substrate and exposure to the atmosphere, undergo in situ chemical reaction resulting in adherent insecticides with controlled release characteristics.

A further object of the present invention is to provide novel compositions containing adhesion promoting, cross-linking reactive silanes and bioactive agents.

These and other objects of the present invention are achieved by using a mixture of (a) a hydrolyzable silane selected from the group consisting of (1) a hydrocarbon substituted hydrolyzable silane, (2) an organopolysiloxane containing hydrolyzable silane groups, and (3) a partial hydrolyzate of (1) and/or (2), and (b) an insecticide.

The hydrolyzable silanes suitable for use in the practice of the present invention have the formula:

$$R_n SiX_{4-n}$$

where R is a monovalent hydrocarbon radical, X is a hydrolyzable group such as halogen, alkoxy, acyloxy, hydrogen and the like, and n is an integer from 0 to 2, inclusive. When X is an alkoxy group, OR', or an acyloxy group, OCOR', R' may be methyl, ethyl, propyl, isopropyl, butyl, isobutyl, secondary butyl, 2-ethylhexyl or other aliphatic hydrocarbon radical of less than 10 carbon atoms. Preferably R' is a lower alkyl radical of no more than 4 carbon atoms. All of the X's may be the same or they may be different. The hydrocarbon radical R may be cyclic or acyclic, saturated or unsaturated, aliphatic or aromatic and include the alkyl, aryl, alkenyl, aralkenyl, cycloalkyl, cycloalkenyl and heterocyclic radicals such as methyl, ethyl, propyl, isopropyl, butyl, isobutyl, secondary butyl, tertiary butyl, amyl, hexyl, vinyl, allyl, chloroallyl, methallyl, crotyl, butadienyl, phenyl, dichlorophenyl, pentachlorophenyl, xylyl, benzyl, styryl, cinnamyl, furfuryl, cyclohexyl, cyclopentadienyl, cyclopentenyl, pyridyl, etc. radicals. The hydrocarbon R may also be a substituted alkyl $R''(CH_2)_x$ where x is an integer from 1 to 20 inclusive and R'' is a polar and/or reactive functionality such as acryloxy, methacryloxy, glycidoxy, epoxycyclohexyl, mercapto, amino, ureido, halo, etc. radicals. There are numerous commercial materials of this type which are commonly known as organofunctional silane coupling agents or adhesion promoters.

The monomeric hydrolyzable silanes may be subjected to partial hydrolysis to promote the formation of condensation products which are still hydrolyzable silanes and are suitable for use in the practice of the present invention.

The organopolysiloxanes containing pendant or terminal hydrolyzable silane radicals, suitable for use in the practice of the present invention, have the formula:

$$P—(SiX_n)_m$$

where P is an organopolysiloxane as hereinafter defined, X is a hydrolyzable group such as halogen, alkoxy, acyloxy, hydrogen, and the like, n is an integer from 2 to 3 and m is an integer from 1 to 20. When X is an alkoxy group OR' or an acyloxy group OCOR', R' may be methyl, ethyl, propyl, isopropyl, butyl, isobutyl, secondary butyl, 2-ethylhexyl or other aliphatic hydrocarbon radical of less than 10 carbon atoms. Preferably, R' is a lower alkyl radical of no more than 4 carbon atoms. All the X's may be the same or they may be different.

The organopolysiloxanes are well known in the art and contain the structural unit:

$$\begin{array}{c} R''' \\ | \\ -Si-O- \\ | \\ R'''' \end{array}$$

where R''' and R'''' are oxygen (i.e., the group —O—) or non-hydrolyzable hydrocarbon, substituted hydrocarbon or heterocyclic radicals and are the same or different. When R''' and R'''' are hydrocarbon radicals, they may be acyclic or cyclic, saturated or unsaturated and include aliphatic radicals such as methyl, ethyl, vinyl, propyl, allyl, butyl, crotyl, hexyl, decyl, dodecyl, hexadecyl, octadecyl, octadecenyl radicals and the like as well as halogenated or other substituted aliphatic radicals, aromatic radicals such as phenyl, biphenyl, phenoxyphenyl and naphthyl radicals as well as halogenated and other substituted aromatic radicals, aralkyl radicals such as benzyl and phenylethyl radicals, alkylaryl radicals such as tolyl and xylyl radicals, cycloaliphatic radicals such as cyclopropyl, cyclopentyl, cyclopentenyl, cyclohexyl and cyclohexenyl radicals and heterocyclic radicals such as furfuryl radicals.

The organopolysiloxanes may be linear, branched or both linear and branched. The polysiloxane may be predominantly a monoorganopolysiloxane, a diorganopolysiloxane, a copolymer containing monoorganosiloxane units and diorganosiloxane units, a copolymer containing triorganosiloxane units and $SiO_2$ units and the like. Notwithstanding the predominant structure, the organopolysiloxane may contain varying amounts of other structural units, in addition to hydrolyzable silane radicals.

The polysiloxanes containing hydrolyzable silane radicals, suitable for use in the practice of the present invention, may be prepared from organopolysiloxanes which are well known in the art. The latter may be prepared by various procedures including controlled hydrolysis of appropriate precursors as well as ring opening polymerization of cyclic organopolysiloxanes.

The controlled hydrolysis and cohydrolysis of $RSiX_3$, $R_2SiX_2$, $R_3SiX$ and $SiX_4$, where X is a hydrolyzable radical as previously defined, yields organopolysiloxane containing monoorganosiloxane, diorganosiloxane, triorganosiloxane and $SiO_2$ units, respectively. The relative proportions of said units in the organopolysiloxane are determined by employing the appropriate proportions of hydrolyzable precursors. In order to be useful in the preparation of polysiloxanes containing hydrolyzable silane radicals, the precursor organopolysiloxanes must be readily soluble or dispersible in organic solvents and contain residual reactive radicals such as hydroxyl, alkoxyl, acyloxyl, halogen, hydrogen, vinyl, allyl and the like.

The polymerization of cyclic organopolysiloxanes provides another route to the preparation of organopolysiloxanes containing reactive radicals which may be employed in the preparation of the organopolysiloxanes containing hydrolyzable silane radicals which are suitable for use in the practice of the present invention. These and other methods of preparation are set forth in K. A. Andrianov, "Metalorganic Polymers", Interscience Publishers, New York, 1965, Chapter III, pages 109–275, the disclosures of which are incorporated herein by reference.

Polysiloxanes which are at an intermediate stage of polymerization in that they contain hydroxyl radicals which, upon application of heat, may undergo condensation to a more advanced stage of polymerization or in that they contain hydrolyzable groups which upon further hydrolysis may proceed to a more advanced stage of polymerization, if they have not been rendered insoluble in organic solvents, are suitable precursors for the preparation of the organopolysiloxanes containing hydrolyzable silanes which may be used in the practice of the present invention.

The organopolysiloxanes containing hydrolyzable silanes may be prepared by reactions well known in the art.

Thus, reaction of an organopolysiloxane containing hydroxyl groups with excess silicon tetraacetate yields the triacetoxysilane as shown by the following reaction:

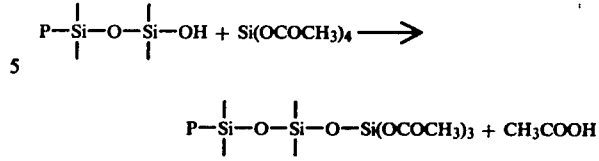

wherein P is as previously defined. Similarly, reaction with an alkyl or aryltriacetoxysilane yields the corresponding diacetoxysilane, as disclosed in U.S. Pat. No. 3,035,016, the disclosure of which is incorporated herein by reference. This reaction is shown below:

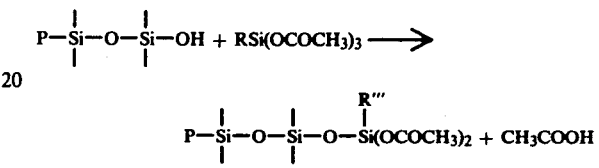

wherein P and R''' are the same as previously defined.

The reaction of an organopolysiloxane containing SiH units, e.g., as prepared by hydrolysis and cohydrolysis of a dichlorosilane with an unsaturated trialkoxysilane or triacyloxysilane in the presence of chloroplatinic acid, yields an organopolysiloxane containing hydrolyzable radicals, suitable for use in the practice of the present invention as shown by the following reaction:

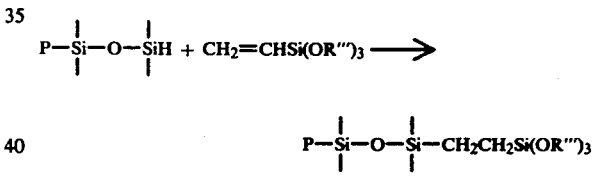

wherein P and R''' are the same as previously defined.

Organopolysiloxanes containing vinyl unsaturation, e.g., as prepared by cohydrolysis of mixtures of various chlorosilanes including vinylalkylchlorosilanes, may be reacted with trialkoxy-silane to yield organopolysiloxanes containing hydrolyzable silane radicals suitable for use in the present invention as shown by the following equation:

P—CH=CH$_2$+HSi(OR''')$_3$→P—CH$_2$—CH$_2$Si(OR''')$_3$ wherein P and R''' are the same as previously described.

Alternative methods of preparing organopolysiloxanes suitable for use in the practice of the present invention will be obvious to those skilled in the art. Notwithstanding the method of preparation, the presence of $SiX_{2-3}$ radicals as pendant or terminal units in an organopolysiloxane renders it suitable for use in the present invention.

The organopolysiloxanes containing hydrolyzable silane radicals may be fluids of low or high viscosity or even solids. The physical appearance of the polysiloxane is dependent upon the nature of the R''' and R'''' radicals, the presence of linear or branched structures as well as the molecular weight. Notwithstanding the physical appearance of the polysiloxane, the important requirement for utility in the practice of the present invention is the presence of hydrolyzable silane radicals. Mixtures of such polysiloxanes are suitable for use in the present invention.

While hydrolyzability is a general characteristic of the silanes which may be used in the practice of the present invention, the rate of hydrolysis is a function of the nature of the hydrocarbon substituent in the hydrolyzable group. Thus, the presence of methyl radicals results in rapid hydrolysis while higher alkyl radicals result in slower hydrolysis. In the latter case, it is possible to use water as a diluent or dispersing medium during the preparation and handling of the active compositions, and as the hydrolyzing reactant as the composition is applied or after it is applied to the substrate.

Insecticides which may be used in the practice of this invention include any of the compounds well known in the art for use as insecticides such as those set forth in Chemical Week, June 21, 1972, pages 39–64; Chemical Week, July 26, 1972, pages 19–41; and Commercial and Experimental Organic Insecticides (1974 Revision), Entomological Society of America, Special Publication 74-1, October 1974. Some common insecticides which may be used include the following:

| | |
|---|---|
| 1-naphthyl methylcarbamate (SEVIN) | pyrethrins |
| malathion | parathion |
| methylparathion | phorate |
| toxaphene | chlordane |
| Dursban | Baygon |
| DDT | Diazinon |

The insecticides which may be used in the practice of this invention also include bacterial insecticides such as *Bacillus popilliae* and *Bacillus thuringiensis* and viral insecticides such as the Heliothis virus. These have been described in Chemical & Engineering News, 35, No. 30, 18 (July 28, 1975), the disclosures of which are incorporated herein by reference.

The insecticide is included in the composition in an amount sufficient to exert an insecticidal action on the immediate environment surrounding the substrate. The amount of insecticide will be dependent upon several factors such as the composition and thickness of the cured polymeric matrix, the nature of the insecticide, i.e., liquid or solid, the presence of active hydrogen functionality, the duration of insecticidal action desired, etc. The optimum amount of insecticide to be included may readily be determined by those skilled in the art. Generally, from about 1 part by weight of insecticide to 0.5 to 1000 parts of hydrolyzable silane is satisfactory.

The compositions of this invention may include volatile diluents such as aliphatic or aromatic hydrocarbons, e.g., Stoddard Solvent, mineral spirits, B&P naphtha, cyclohexane, petroleum ether, benzene, toluene, xylene, etc., halogenated hydrocarbons such as perchloroethylene and fluorocarbons or volatile fluid polysiloxanes such as dimethylpolysiloxane fluids. The compositions may be prepared by merely admixing the various components. Before admixing, the components may be dispersed or dissolved in a diluent such as previously described. The compositions may also be prepared in aqueous media when slowly hydrolyzing and/or stable components are present.

The compositions of this invention may be applied to a large number of substrates. The substrate should be one which contains active hydrogen atoms which provide sites for coupling with the hydrolyzable silane system, e.g., hydroxyl groups, amino groups, etc. Thus, various plants such as ornamental bushes, trees, flowers, greenhouse plants, lawns, crops (e.g., wheat, corn, soy beans, barley, oats, cotton, jute, sisle), fruits, vegetables, berry bushes, nut trees, olive trees, fig trees, grape vines; various animals such as household pets (e.g., cats, dogs), farm animals such as dairy cattle, beef cattle, horses, sheep, chickens, turkeys, swine, goats, zoo animals, etc. Non-plant and animal uses include spraying surfaces of structures such as buildings and various rooms in buildings, such as kitchens, bathrooms, closets including wood or plaster board walls and floor tile to protect against roaches, termites, flying insects, rug insects, ants, etc. Various containers such as bags and cardboard or wooden boxes may also serve as substrates in accordance with the practice of this invention.

The compositions of this invention may be applied to the substrate by brushing, spraying, dipping or any other known technique for applying a fluid composition to a solid substrate. It may be applied in the form of an aerosol mist or fog, propelled by conventional pressurized volatile halohydrocarbon, hydrocarbon or compressed gas propellants, an air propelled mist blower, a fog generator, or other suitable means.

Although this invention should not be limited thereby, it is believed that upon application of the compositions of this invention to a suitable substrate in an ambient atmosphere, evaporation of the volatile diluent, if any is present, and exposure to atmospheric moisture results in the hydrolysis of the hydrolyzable silane, followed by condensation of the $Si(OH)_y$ groups generated thereby to form a crosslinked organopolysiloxane matrix containing entrapped or occluded insecticide. Simultaneously, the $Si(OH)_y$ groups promote the adhesion of the polysiloxane matrix and the insecticide entrapped or occluded therein to the substrate. Adhesion to the substrate is due at least in part to the fact that the polysiloxane matrix is coupled to the substrate by reaction through active hydrogen atoms on the substrate. Thus, the insecticide is held on the substrate to such an extent that it cannot be physically brushed off, blown off, or washed off by rain. Further, as a result of the entrapped condition, the rapid evaporation, sublimation or extraction of the insecticide is retarded. However, due to the permeability of the organopolysiloxane to organic compounds, said evaporation or sublimation is not completely inhibited, resulting in controlled release of the insecticide.

When water is present in the compositions of this invention, said water is generally added shortly before application of the composition to a suitable substrate, and hydrolysis of the silane may begin before or during application to said substrate. However, hydrolysis continues after said application and is followed by condensation of the SiOH groups generated thereby.

The rate of crosslinking of the hydrolyzable silane, after moisture induced hydrolysis, may be increased by the use of catalysts, such as tin soaps including stannous octoate and dibutyl tin dilaurate. Thus, the volatility of a low viscosity, low molecular weight alkoxysilane such as methyl triethoxysilane or tetraethyl orthosilicate, may result in loss by evaporation before sufficient hydrolysis followed by condensation can increase the viscosity and retard evaporation. The rate of condensation is increased in the presence of a catalyst, resulting in a rapid viscosity increase and decreased volatility.

The rate of release of the insecticide may be controlled by controlling the thickness of the organopolysiloxane coating, e.g., by modifying the concentration of components in the solution thereof, or by adding a nonvolatile, non-reactive extender for the crosslinked polysiloxane. The latter acts in a manner analogous to the behavior of the hydrocarbon oil in a vulcanized oil-extended hydrocarbon rubber. The extender may be a compatible non-siloxane compound, e.g., a hydrocarbon oil, or may be an alkyl or arylpolysiloxane fluid having a viscosity ranging from 5 to 100,000 centistokes at 25° C.

In addition to or in lieu of the solvents which function to reduce the viscosity of the compositions of this invention as well as control the thickness of the polysiloxane coating, volatile alcohols such as ethanol, isopropanol, butanol and the like may be included in the composition to prevent premature hydrolysis of the hydrolyzable crosslinking agent with resultant gelation and precipitation.

Other additives which may be incorporated into the compositions of this invention include stabilizers against environmental degradation, such as antioxidants and ultraviolet stabilizers, odor masking compounds and perfumes, dyes, pigments, fillers, etc.

The following examples illustrate the best modes for carrying out this invention. Example I illustrates the preparation of a hydrolyzable silane. Example II illustrates the improved adhesion of a composition of this invention to a substrate. In the tables, the numbers refer to the amount of materials in parts by weight.

EXAMPLE I

Triethoxysilylethylated Methylhydrogenpolysiloxane

A 250 ml. 3-necked flask equipped with a stirrer, thermometer, dropping funnel, condenser and nitrogen inlet was charged under nitrogen with 160 g. (0.07 mole) of a methylhydrogenpolysiloxane, containing 35 methylhydrogensiloxy units and 2 trimethylsiloxy terminal units, and 0.27 g. chloroplatinic acid. A total of 53.9 g. (0.28 mole) of vinyltriethoxysilane was added over a period of 1 hour to the reaction mixture which had been heated to 80° C. The temperature rose and was maintained at 110° C. for an additional hour. The reaction mixture was cooled to 25° C. and filtered under nitrogen to remove the black catalyst particles. The filtrate was kept at 25° C. at 0.1 mm. pressure for 20 hours to remove residual vinyltriethoxysilane. The product was obtained in a yield of 92% and was analyzed for ethoxy content by acetylation and hydrolysis, in accordance with the procedures of A. L. Smith, "Analysis of Silicones", Wiley-Interscience, 1974, p. 154. The triethoxysilylethylated methylhydrogenpolysiloxane had an ethoxy content of 14.3 weight-%.

EXAMPLE II

Solutions containing 50 weight-% of the triethoxysilylethylated methylhydrogenpolysiloxane (TESEPS) of Example I and/or a dimethylpolysiloxane fluid, designated as a DC-200 fluid by the Dow Corning Corp., having a viscosity of 1000 centistokes at 25° C. (DC-200/1000), were prepared in anhydrous isooctane.

The 50% solutions of TESEPS and/or polysiloxane fluid in isooctane were mixed with a pyrethroid composition as follows:
0.1 g. pyrethroids
0.5 g. piperonyl butoxide
0.4 g. petroleum distillate
5.0 g. 50% solution of TESEPS and/or DC-200/1000 in isooctane The pyrethroid-containing solutions were diluted to 10 weight-% with isooctane and 10–20 drops were placed on a weighed glass slide. A glass rod was rolled over the solution to spread the material uniformly over the lower four fifths of the slide. The coated slide was air dried for 4 hours and then placed in a 50% relative humidity chamber for 18 hours. The slide was then weighed to determine the weight of the coating which ranged from 2–5 mg. covering an area of 15 sq. cm. The coated slide was inserted into a slit rubber stopper and mounted over the center of a Waring Blender. The coated slide faced the moving water which completely covered the coating. The blender was operated at its highest speed for 5 minutes. The slide was air dried overnight and then weighed to determine the amount of coating retained on the slide after the treatment in the Blender. The average results of duplicate tests are summarized in Table 1, where the amount of pyrethroids indicated actually represents the sum of the pyrethroids and piperonyl butoxide.

Table 1

| No. | Adhesion of Pyrethroids-TESEPS Compositions | | | |
|---|---|---|---|---|
| | TESEPS | DC-200/1000 | Pyrethroids | Retention, % |
| 1 | | | 100 | 0 |
| 2 | | 100 | 24 | 4 |
| 3 | 100 | | 24 | 12 |
| 4 | 50 | 50 | 24 | 11 |

The hydrolysis of triethoxysilylethylated polysiloxane results in crosslinking of the polymer and its adhesion to the substrate.

EXAMPLE III

Solutions containing 50 weight-% of one or more of the following components were prepared in anhydrous isooctane: (a) methyltriethoxysilane, designated as A-162 by Union Carbide Corp., (b) tetraethyl orthosilicate (ES-100), and (c) dimethylpolysiloxane fluid DC-200/1000.

The solutions were diluted, coated on glass slides, dried, moisture cured at 50% relative humidity for 18 hours and subjected to treatment with water in the Waring Blender as described in Example II. The results are summarized in Table 2.

Table 2

| No. | Adhesion of Silane Compositions | | | |
|---|---|---|---|---|
| | A-162 | ES-100 | DC-200/1000 | Retenton, % |
| 5 | | | 100 | 44 |
| 6 | | 100 | | 0 |
| 7 | 100 | | | 0 |
| 8 | | 50 | 50 | 50 |
| 9 | 50 | | 50 | 53 |
| 10 | | 100* | | 78 |
| 11 | 100* | | | 85 |

*Catalyzed with 2 weight-% stannous octoate

The volatility and slow hydrolysis of the methyltriethoxysilane (No. 7) and tetraethyl orthosilicate (No. 6) result in poor crosslinking and low retention. The presence of the viscous polysiloxane fluid (Nos. 8 and 9) retards volatilization. In the presence of the catalyst (Nos. 10 and 11) the rate of crosslinking is increased and adhesion is promoted.

EXAMPLE IV

A solution containing 50 weight-% non-volatiles was prepared as follows:
- 10 g. triethoxysilylethylated methylhydrogenpolysiloxane (14 wt-% $OC_2H_5$) of Example I (TESEPS)
- 40 g. DC-200/1000 dimethylpolysiloxane fluid
- 50 g. perchloroethylene The polysiloxanylalkoxysilane-dimethylpolysiloxane solution was mixed with a pyrethroid composition to yield an insecticide-containing solution which was compared with an additive-free pyrethroid composition for insecticidal behavior. The components of the test compositions were as follows:

|  | Insecticide Solution | |
| --- | --- | --- |
|  | IVA | IVB |
| Pyrethroids | 0.1 | 0.1 |
| Piperonyl butoxide | 0.5 | 0.5 |
| Petroleum distillate | 0.4 | 0.4 |
| TESEPS | 1.0 | — |
| DC-200/1000 | 4.0 | — |
| Perchloroethylene | 94.0 | 99.0 |

A disposable plastic syringe was used to place the test solution on a 4×4 inch glass panel. The solution was uniformly spread over the panel with the tip of the syringe. The treated panels were conditioned for 24 hours in a chamber at 78° F. and 48% relative humidity. Ten adult male German cockroaches, *Blattella germanica* (Linnaeus), were exposed to the 1 day residue for 24 hours under a 100×15 mm. petri dish. The test was conducted in duplicate. The same treated panels were reexposed to cockroaches after 3, 7 and 10 days.

The percent mortality of cockroaches exposed to the treated glass panels is summarized below:

| Insecticide Solution | | |
| --- | --- | --- |
| Residue age | IVA | IVB |
| 1 day | 100 | 100 |
| 3 days | 100 | 100 |
| 7 days | 65 | 0 |
| 10 days | 75 | 0 |

The residue from the control insecticide solution IVB was ineffective after 7 days while the residue from insecticide solution IVA, containing the polysiloxanylalkoxysilane-dimethylpolysiloxane fluid composition, killed 65% of the exposed cockroaches after 7 days and 75% after 10 days.

On the 11th day the panel containing the residue from solution IVA as subjected to treatment with water in a Waring Blender for 5 min., as described in Example II, and then reexposed to cockroaches after a total residue age of 15 days. On the 16th day, the panel was again subjected to treatment with water in a Waring Blender for 5 min. and then reexposed to cockroaches after a total residue age of 18 days.

The percent mortality of cockroaches exposed to the treated glass panels is summarized below:

|  | Insecticide Solution |
| --- | --- |
| Residue age | IVA |
| 11 days - water treatment | |
| 15 days | 55 |
| 16 days - water treatment | |
| 18 days | 25 |

It is apparent that even after a vigorous water treatment, the residue from insecticide solution IVA killed 55% of the exposed cockroaches after 15 days. After an additional water treatment, the residue from solution IVA still killed 25% of the exposed cockroaches after 18 days.

EXAMPLE V

The following solutions containing 50 weight-% of active components were prepared in anhydrous isooctane: (a) dimethylpolysiloxane fluid DC-200/1000, and (b) methyltriethoxysilane (A-162), DC-200/1000 fluid and stannous octoate in 20/80/0.1 weight ratio.

The 50% solutions were mixed with a pyrethroid composition as follows:
- 0.1 g. pyrethroids
- 0.5 g. piperonyl butoxide
- 0.4 g. petroleum distillate
- 5.0 g. 50% solution of DC-200/1000 or A-162—DC-200/1000—stannous octoate in isooctane The pyrethroid-containing solutions were coated on glass slides, dried, moisture cured at 50% relative humidity for 18 hours and subjected to treatment with water in the Waring Blender, as described in Example II. The averaged results of duplicate tests are summarized in Table 3, where the amount of pyrethroids indicated actually represents the sum of the pyrethroids and piperonyl butoxide.

Table 3

| Adhesion of Pyrethroids-Silane Compositions | | | | |
| --- | --- | --- | --- | --- |
| No. | A-162 | DC-200/1000 | Pyrethroids | Retention, % |
| 1 |  |  | 100 | 0 |
| 2 |  | 100 | 24 | 4 |
| 12 | 20* | 80 | 24 | 38 |

*Catalyzed with 0.5 weight-% stannous octoate

EXAMPLE VI

A solution containing 50 weight-% non-volatiles was prepared as follows:
- 10 g. methyltriethoxysilane (A-162)
- 40 g. DC-200/1000 dimethylpolysiloxane fluid
- 0.025 g. stannous chloride
- 50 g. perchloroethylene The alkoxysilane-dimethylpolysiloxane-stannous octoate solution was mixed with a pyrethroid composition to yield an insecticide-containing solution which was compared with an additive-free pyrethroid composition for insecticidal behavior. The components of the test compositions were as follows:

|  | Insecticide Solution | |
| --- | --- | --- |
|  | VIA | VIB |
| Pyrethroids | 0.1 | 0.1 |
| Piperonyl butoxide | 0.5 | 0.5 |
| Petroleum distillate | 0.4 | 0.4 |
| A-162 | 1.0 | — |
| DC-200/1000 | 4.0 | — |
| Stannous octoate | 0.0025 | — |

|  | Insecticide Solution | |
|---|---|---|
|  | VIA | VIB |
| Perchloroethylene | 94.0 | 99.0 |

The insecticidal properties of solutions VIA and VIB were evaluated using adult cockroaches as the test species and glass as the test surface, as described in Example IV. The treated glass panels were exposed, in duplicate, to cockroaches after 1, 3, 7 and 10 days.

The percent mortality of cockroaches exposed to the treated glass panels is summarized below:

|  | Insecticide Solution | |
|---|---|---|
| Residue Age | VIA | VIB |
| 1 day | 100 | 100 |
| 3 days | 100 | 100 |
| 7 days | 100 | 0 |
| 10 days | 50 | 0 |

The residue from the control insecticide solution VIB was ineffective after 7 days while the residue from insecticide solution VIA, containing the alkoxysilane-dimethylpolysiloxane fluid composition, killed 100% of the exposed cockroaches after 7 days and 50% after 10 days.

On the 11th day the panel containing the residue from solution VIA was subjected to treatment with water in a Waring Blender for 5 min., as described in Example II, and then reexposed to cockroaches after a total residue age of 15 days. On the 16th day, the panel was again subjected to treatment with water in a Waring Blender for 5 min. and then reexposed to cockroaches after a total residue age of 18 days.

The percent mortality of cockroaches exposed to the treated glass panels is summarized below:

|  | Insecticide Solution |
|---|---|
| Residue Age | VIA |
| 11 days - water treatment | |
| 15 days | 45 |
| 16 days - water treatment | |
| 18 days | 25 |

The residue from insecticide solution VIA was still effective and killed 45% of the exposed cockroaches after 15 days, despite a vigorous water treatment after 11 days. The residue still killed 25% of the exposed cockroaches after 18 days, despite another water treatment after 16 days.

EXAMPLE VII

A solution containing 50 weight-% non-volatiles was prepared as follows:
15 g. methyltriethoxysilane (A-162)
15 g. DC-200/1000 dimethylpolysiloxane fluid
30 g. perchloroethylene The alkoxysilane-dimethylpolysiloxane solution was mixed with a pyrethroid composition to yield an insecticide-containing solution which was compared with an additive-free pyrethroid composition for insecticidal behavior. The components of the test compositions were as follows:

|  | Insecticide Solution | |
|---|---|---|
|  | VIIA | VIIB |
| Pyrethroids | 0.1 | 0.1 |
| Piperonyl butoxide | 0.5 | 0.5 |
| Petroleum distillate | 0.4 | 0.4 |
| A-162 | 0.25 | — |
| DC-200/1000 | 0.25 | — |
| Perchloroethylene | 98.5 | 99.0 |

The insecticidal properties of solutions VIIA and VIIB were evaluated using adult cockroaches as the test species and glass as the test surface, as described in Example IV. The treated glass panels were exposed, in duplicate, to cockroaches after 1, 3, 7 and 10 days.

The percent mortality of cockroaches exposed to the treated glass panels is summarized below:

|  | Insecticide Solution | |
|---|---|---|
| Residue Age | VIIA | VIIB |
| 1 day | 100 | 100 |
| 3 days | 100 | 100 |
| 7 days | 85 | 0 |
| 10 days | 70 | 0 |

The residue from the control insecticide solution VIIB was ineffective on the 7th day while the residue from insecticide solution VIIA, containing the alkoxysilane-dimethylpolysiloxane fluid composition, killed 85% of the exposed cockroaches after 7 days and 70% after 10 days.

What is claimed is:

1. A composition capable of undergoing hydrolysis under ambient conditions to form a polymeric network capable of controlling the release of an insecticide consisting essentially of (a) a hydrolyzable silane selected from the group consisting of (1) a hydrocarbon substituted hydrolyzable silane, and (2) an organopolysiloxane containing hydrolyzable silane groups, or a partial hydrolyzate thereof, and (b) an insecticide.

2. The composition of claim 1 wherein the hydrocarbon substituted hydrolyzable silane has the formula $R_nSiX_{4-n}$ where R is a monovalent hydrocarbon radical, X is a hydrolyzable group selected from the group consisting of halogen, alkoxy, acyloxy and hydrogen, and n is an integer from 0 to 2.

3. The composition of claim 1 wherein the organopolysiloxane containing hydrolyzable silane groups has the formula $P\text{---}(SiX_n)_m$ where P is an organopolysiloxane, X is a hydrolyzable group selected from the group consisting of halogen, alkoxy, acyloxy and hydrogen, n is an integer from 2 to 3, and m is an integer from 1 to 20.

4. The composition of claim 3 wherein the organopolysiloxane contains the structural unit:

wherein R''' and R'''' are oxygen or non-hydrolyzable hydrocarbon or heterocyclic radicals.

5. The composition of claim 4 wherein the non-hydrolyzable radicals are selected from the group consisting of acyclic or cyclic, saturated or unsaturated aliphatic radicals, aromatic radicals, aralkyl radicals and alkylaryl radicals.

6. A composition capable of undergoing hydrolysis under ambient conditions to form a polymeric network capable of controlling the release of an insecticide consisting essentially of (a) a hydrolyzable silane selected from the group consisting of (1) an organopolysiloxane containing hydrolyzable silane groups, or a partial hydrolyzate thereof, (b) a non-volatile, non-reactive hydrocarbon oil or organopolysiloxane, and (c) an insecticide.

7. A composition capable of undergoing hydrolysis under ambient conditions to form a polymeric network capable of controlling the release of an insecticide consisting essentially of (a) a hydrolyzable silane selected from the group consisting of (1) a hydrocarbon substituted hydrolyzable silane, and (2) an organopolysiloxane containing hydrolyzable silane groups, or a partial hydrolyzate thereof, (b) an insecticide, and (c) a volatile diluent selected from the group consisting of aliphatic or aromatic hydrocarbons, halogenated hydrocarbons, organopolysiloxane fluids, and water.

8. A composition capable of undergoing hydrolysis under ambient conditions to form a polymeric network capable of controlling the release of an insecticide consisting essentially of (a) a hydrolyzable silane selected from the group consisting of (1) a hydrocarbon substituted hydrolyzable silane, and (2) an organopolysiloxane containing hydrolyzable silane groups, or a partial hydrolyzate thereof, (b) a non-volatile, non-reactive hydrocarbon oil or organopolysiloxane, (c) an insecticide, and (d) a volatile diluent selected from the group consisting of aliphatic or aromatic hydrocarbons, halogenated hydrocarbons, organopolysiloxane fluids and water.

9. A process for providing a substrate containing active hydrogen atoms with an adherent controlled release pesticide which comprises applying the composition of claim 1 to said substrate and exposing the coated substrate to atmospheric moisture.

10. A process for providing a substrate containing active hydrogen atoms with an adherent controlled release pesticide which comprises applying the composition of claim 2 to said substrate and exposing the coated substrate to atmospheric moisture.

11. A process for providing a substrate containing active hydrogen atoms with an adherent controlled release pesticide which comprises applying the composition of claim 3 to said substrate and exposing the coated substrate to atmospheric moisture.

12. A process for providing a substrate containing active hydrogen atoms with an adherent controlled release pesticide which comprises applying the composition of claim 4 to said substrate and exposing the coated substrate to atmospheric moisture.

13. A process for providing a substrate containing active hydrogen atoms with an adherent controlled release pesticide which comprises applying the composition of claim 5 to said substrate and exposing the coated substrate to atmospheric moisture.

14. A process for providing a substrate containing active hydrogen atoms with an adherent controlled release pesticide which comprises applying the composition of claim 6 to said substrate and exposing the coated substrate to atmospheric moisture.

15. A process for providing a substrate containing active hydrogen atoms with an adherent controlled release pesticide which comprises applying the composition of claim 7 to said substrate and exposing the coated substrate to atmospheric moisture.

16. A process for providing a substrate containing active hydrogen atoms with an adherent controlled release pesticide which comprises applying the composition of claim 8 to said substrate and exposing the coated substrate to atmospheric moisture.

17. A process as defined in claim 9 wherein said substrate is a plant.

18. A process as defined in claim 9 wherein said substrate is an animal.

19. A process as defined in claim 9 wherein said substrate is the surface of a structure.

* * * * *